(12) United States Patent
Feingold et al.

(10) Patent No.: US 9,186,245 B2
(45) Date of Patent: Nov. 17, 2015

(54) LENS INJECTOR APPARATUS AND METHOD (76) Inventors: Vladimir Feingold, Laguna Niguel, CA (US); Ioannis Pallikaris, Crete (GR)

( * ) Notice: Subject to any disclaimer, the term of this patent is extended or adjusted under 35 U.S.C. 154(b) by 106 days.

(21) Appl. No.: 13/226,918

(22) Filed: Sep. 7, 2011

(65) Prior Publication Data
US 2013/0060255 A1 Mar. 7, 2013

(51) Int. Cl.
*A61F 2/16* (2006.01)
*A61F 2/14* (2006.01)

(52) U.S. Cl.
CPC ............. *A61F 2/167* (2013.01); *A61F 2/148* (2013.01)

(58) Field of Classification Search
CPC ....... A61F 2/148; A61F 2/1664; A61F 9/013; A61F 9/0017; A61F 9/0061; A61F 2/167; A61F 2/1662
USPC ............ 606/107; 623/4.1, 5.11, 6.12; 604/11, 604/15, 38, 294–302
See application file for complete search history.

(56) References Cited

U.S. PATENT DOCUMENTS

| | | | |
|---|---|---|---|
| 4,880,000 A | | 11/1989 | Holmes et al. |
| 6,398,277 B1 * | | 6/2002 | McDonald ................. 294/1.2 |
| 2006/0064112 A1 * | | 3/2006 | Perez ........................ 606/107 |
| 2008/0243138 A1 * | | 10/2008 | Dishler et al. ............. 606/107 |
| 2008/0275462 A1 | | 11/2008 | Feingold et al. |
| 2011/0196381 A1 | | 8/2011 | Feingold |

OTHER PUBLICATIONS

International Search Report and the Written Opinion of the International Searching Authority of PCT/US2012/053733 filed Sep. 5, 2012.

* cited by examiner

*Primary Examiner* — Sarah W Aleman
(74) *Attorney, Agent, or Firm* — Andres F. Arrubla; Victor Siber (57) ABSTRACT

An embodiment in accordance with the present invention provides an apparatus and method for injecting a lens into a flap or pocket in the cornea. This lens or pocket preferably is created by a laser used in conventional lasik surgery. The apparatus includes a syringe or handle, a plunger extending movably through the lumen of the syringe, and a paddle. The paddle extends from the distal end of the syringe and is configured to hold the lens to be injected into the eye. The paddle also defines a fluid flow path in fluid communication with the lumen of the syringe and configured to allow saline to flow onto the paddle to lift the lens from the paddle, such that the lens can be inserted into the eye.

14 Claims, 7 Drawing Sheets

LENS INJECTOR APPARATUS AND METHOD

FIELD OF THE INVENTION

The present invention relates generally to ocular surgery. More particularly, the present invention relates to an apparatus and method for injecting a lens into the eye to treat presbyopia.

BACKGROUND OF THE INVENTION

Presbyopia is the gradual loss of near vision, which often accompanies the aging process. The eyes of a person suffering from presbyopia have a diminished ability to focus on near objects such as books, magazines, or a computer screen. Symptoms of presbyopia can include difficulty reading fine print and blurred vision when transitioning the focus of the eye between near and distant objects.

There are several common treatments for presbyopia. A dedicated pair of reading glasses is one such treatment. Reading glasses provide magnification of near objects to provide for improved vision. However, if a person also needs glasses to focus on distant objects switching between reading glasses and distance glasses can be inconvenient. Another treatment is bifocal glasses, which provide a portion of the glasses lens for assisting with distance vision and a portion for assisting with near vision. While bifocals provide a single pair of glasses for both near and distance vision correction, they can cause disorientation. Contact lenses for the surface of the eye have also been developed which provide vision correction for both near and distance vision. Although these treatments provide vision correction for a person suffering from presbyopia, each requires at least one an additional accessory or pair of contact lenses that must be worn or used daily. Additionally, very small lenses for insertion into the eye are being developed. However, these lenses cannot be handled manually or with conventional tools.

Accordingly, it is desirable to provide an apparatus and method for inserting a lens into the cornea to improve a patient's presbyopia.

SUMMARY OF THE INVENTION

The foregoing needs are met, to a great extent, by the present invention, wherein in one aspect an apparatus is provided that in some embodiments includes a design for a lens injector apparatus and method.

In accordance with one aspect of the present invention, an apparatus for injecting a lens into an eye includes a syringe having a distal end and a proximal end. An outer wall of the syringe can define a lumen extending through the handle, and the lumen of the syringe can be configured to hold saline. A plunger can extend movably through the lumen of the syringe and can have a distal end and a proximal end. The plunger can also be configured to eject the saline from the lumen of the syringe. A paddle can extend from the distal end of the syringe and can be configured to hold the lens to be inserted into the eye. The paddle can also define a fluid flow path in fluid communication with the lumen of the syringe and configured to allow saline to flow onto the paddle to lift the lens from the paddle such that the lens can be inserted into the eye.

In accordance with another aspect of the present invention, the paddle can include a fill channel defining the fluid flow path on the paddle and a flood channel configured to fill with saline. The fill channel can be configured to extend to the flood channel such that the fill channel and the flood channel are in fluid communication. The flood channel can also include concentric flood channels, and therefore, the fill channel can be configured to extend through the concentric flood channels such that the fill channel and the flood channels are in fluid communication. Additionally, the paddle can be configured such that the lens nests on a top surface of the paddle.

In accordance with another aspect of the present invention, an apparatus for injecting a lens into a corneal pocket or flap includes a handle having a distal end and a proximal end. The handle can also include an outer wall defining a lumen extending through the handle. The apparatus can also include a plunger extending movably through the lumen of the handle having a distal end and a proximal end. A paddle having a proximal end and a distal end can extend from the distal end of the handle. The paddle can include a tubular portion positioned at the proximal end of the paddle, wherein the tubular portion defines an inner lumen in fluid communication with the inner lumen of the handle. The paddle can also include a generally flat disc portion configured to hold the lens to be inserted into the eye wherein the disc portion is in fluid communication with the tubular portion. Additionally, the paddle can be configured to allow saline to flow onto the flat disc portion of the paddle to lift the lens, such that the lens can be inserted into the corneal pocket or flap.

In accordance with still another aspect of the present invention, the paddle can include a fill channel defining the fluid flow path on the paddle and a flood channel configured to fill with saline. The fill channel can be configured to extend to the flood channel such that the fill channel and the flood channel are in fluid communication. The flood channel can also include concentric flood channels, and therefore, the fill channel can be configured to extend through the concentric flood channels such that the fill channel and the flood channels are in fluid communication. Additionally, the paddle can be configured such that the lens nests on a top surface of the paddle.

In accordance with yet another aspect of the present invention, a method for injecting a lens into a corneal pocket or flap can include positioning a lens on a paddle disposed at a distal end of a device for injecting the lens into the corneal flap or pocket. The method can also include injecting the lens into a corneal flap or pocket. Additionally, the method can include, positioning the paddle in the corneal flap or pocket and depressing a plunger of the device for injecting the lens into the corneal flap or pocket to dispense saline onto the paddle such that the saline lifts the lens off of the paddle. The method can also include removing the paddle from the pocket, such that the lens remains in position in the corneal flap or pocket.

In accordance with another aspect of the present invention, the method can include filling a fill channel defined by the paddle with Balanced Salt Solution (BSS) or saline. The method can also include filling a flood channel in fluid communication with the fill channel with Balanced Salt Solution (BSS) or saline, wherein the flood channel can include concentric flood channels. The method can also include nesting the lens on a top surface of the paddle. Additionally, the method can include creating a Balanced Salt Solution (BSS) or saline droplet on the top surface of the paddle between the top surface of the paddle and the lens.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

The invention will now be described with reference to the drawing figures, in which like reference numerals refer to like parts throughout. An embodiment in accordance with the present invention provides an apparatus and method for injecting a lens into a flap or pocket in the cornea. This lens or pocket preferably is created by a laser used in conventional Lasik surgery. The apparatus includes a syringe or handle, a plunger extending movably through the lumen of the syringe, and a paddle. The paddle extends from the distal end of the syringe and is configured to hold the lens to be injected into the eye. The paddle also defines a fluid flow path in fluid communication with the lumen of the syringe and configured to allow saline to flow onto the paddle to lift the lens from the paddle, such that the lens can be inserted into the eye.

Figure 1:
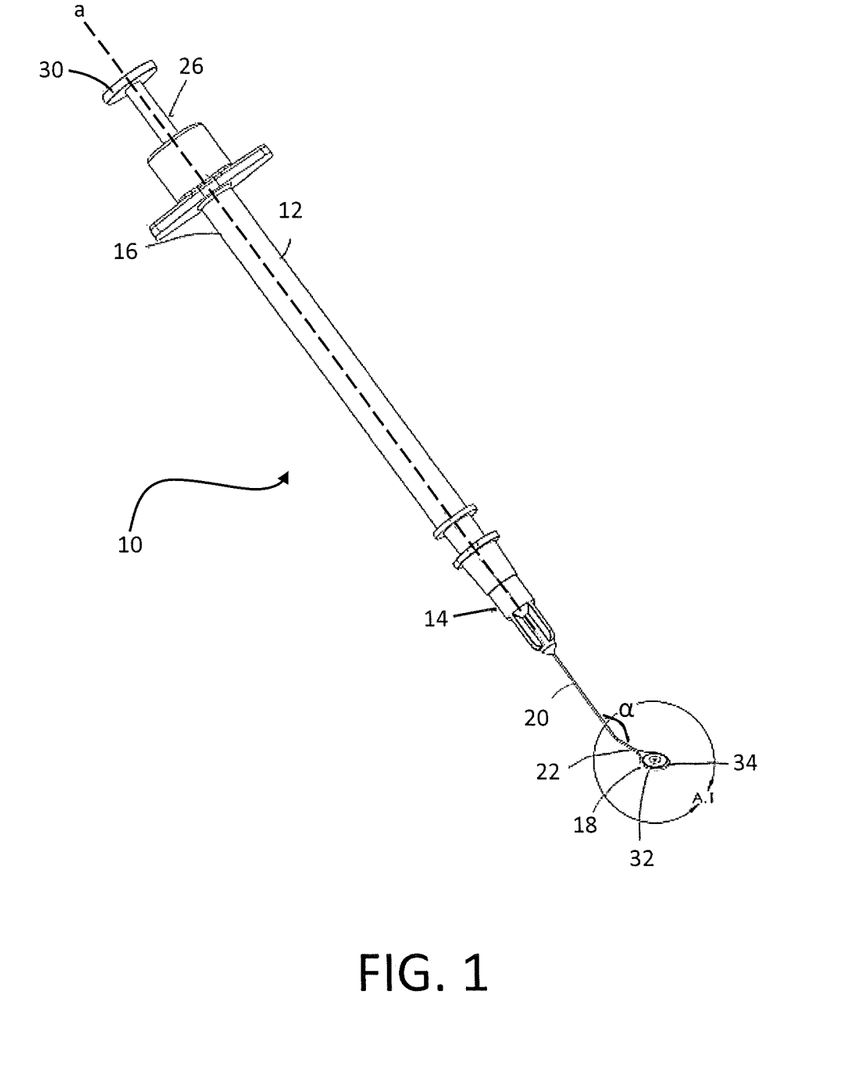
FIG. 1 illustrates a perspective view of a lens injector apparatus in accordance with an embodiment of the invention.
Figure 2:
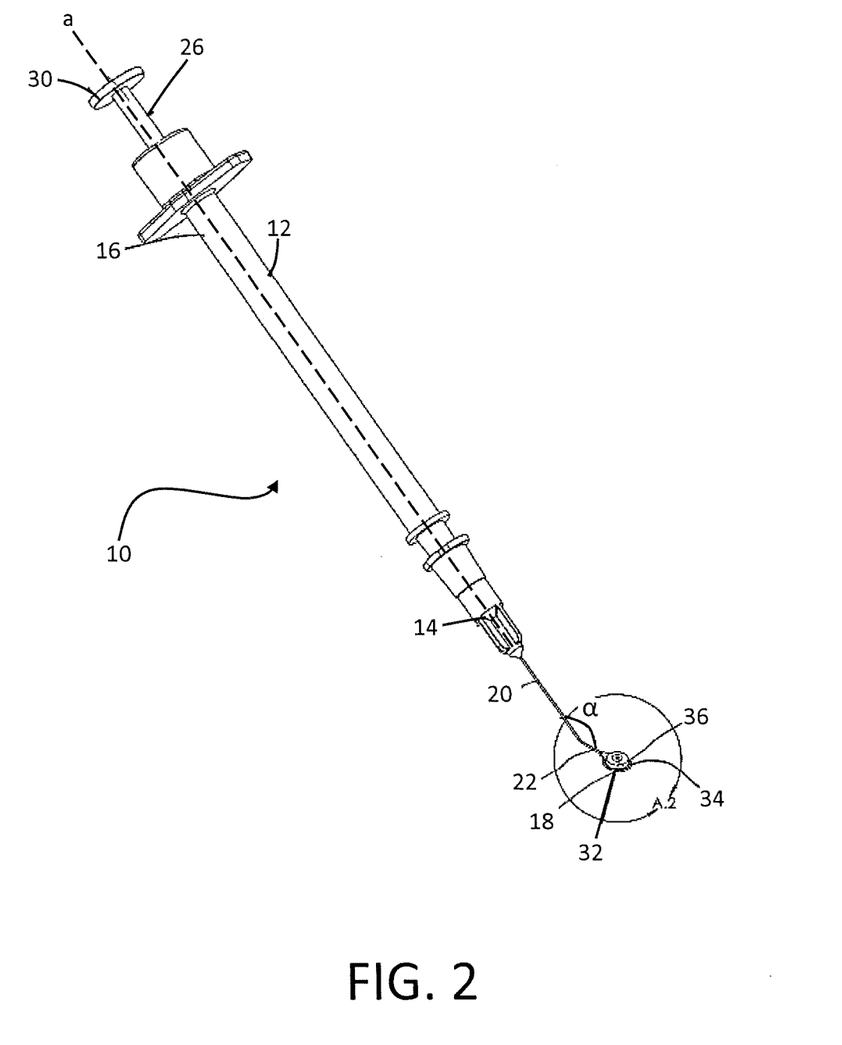
FIG. 2 illustrates a perspective view of a lens injector apparatus in accordance with an embodiment of the invention.

An embodiment of the present inventive apparatus is illustrated in FIGS. 1 and 2. FIGS. 1 and 2 illustrate a perspective view of a lens injector apparatus 10 in accordance with an embodiment of the invention. The lens inserter apparatus 10 includes a syringe or handle 12, which has a distal end 14 and a proximal end 16. The lens inserter 10 also includes a paddle 18 disposed on a paddle arm 20, which extends from the distal end 14 of the handle 12. Preferably, the paddle 18 has a length in a range of 10 mm to 30 mm and a width in a range of 2 mm to 8 mm. The paddle 18 has a thickness in a range of 100 microns to 400 microns. The paddle 18 can be formed from plastic or any other suitable material. The paddle 18 is disposed at a distal end 22 of the paddle arm 20. The paddle arm 20 is bent at an angle α which is in the range of 100° to 160°. Additionally, a plunger 26 extends through the syringe 12. The plunger can be formed from metal or plastic or any other suitable non corrosive material. A finger rest 30 is coupled to the plunger 26. The finger rest 30 can be used to move the plunger 28 through the lumen of the syringe 12. The lens inserter apparatus 10 also includes a longitudinal axis FIG. 1 also illustrates the lens injector 10 in its resting, loaded state. A lens 32 is disposed on a top surface 34 of the paddle 18. The paddle 18 can be configured such that the lens 32 nests within a depression 36 on the top surface 34 of the paddle 18. FIG. 2 also illustrates the lens injector 10 after the plunger 26 has been depressed. As the plunger 26 is depressed, Balanced Salt Solution (BSS) or saline is dispensed on the top surface 34 of the paddle 18. A Balanced Salt Solution (BSS) or saline droplet 38 is formed on the top surface 34 of the paddle 18, lifting the lens 32 off of the top surface 34 of the paddle 18.

Figure 3:
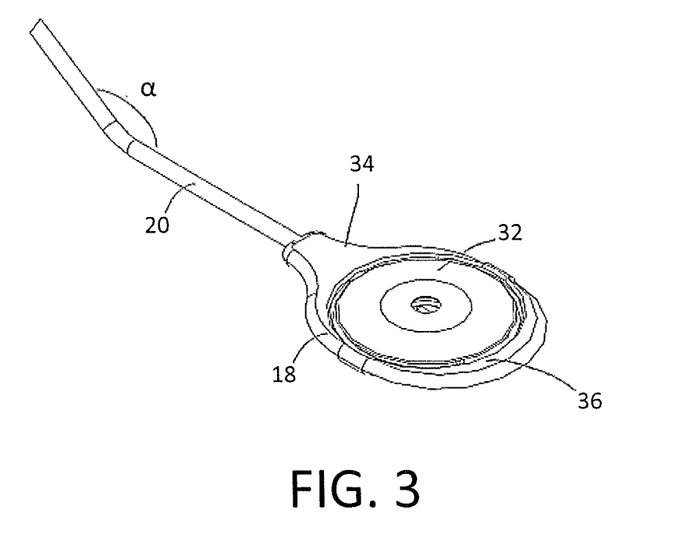
FIG. 3 illustrates a view of the distal end of the lens injector illustrated in FIG. 1.
Figure 4:
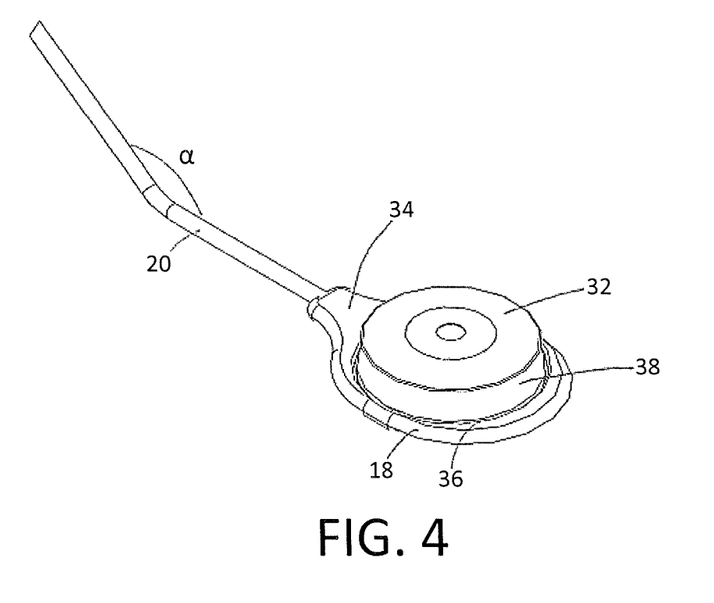
FIG. 4 illustrates a view of the distal end of the lens injector illustrated in FIG. 2.

FIGS. 3 and 4 illustrate a view of the distal end of the lens injector as shown in FIGS. 1 and 2. FIGS. 3 and 4 illustrate a lens 32 disposed on the paddle 18. Preferably, the lens 32 is approximately 2.5 mm to 3.5 mm in diameter and has an edge thickness of less than 20 microns. Although, any lens suitable for insertion into a pocket or flap in a cornea can be used. FIG. 3 illustrates the lens injector 10 in its resting, loaded state. The lens 32 is disposed on a top surface 34 of the paddle 18. The paddle 18 can be configured such that the lens 32 nests within a depression 36 on the top surface 34 of the paddle 18. FIG. 4 illustrates the lens injector 10 after the plunger 26 has been depressed. As the plunger 26 is depressed, saline is dispensed on the top surface 34 of the paddle 18. This forms a saline droplet 38 on the top surface 34 of the paddle 18, lifting the lens 32 off of the top surface 34 of the paddle 18.

Figure 5:
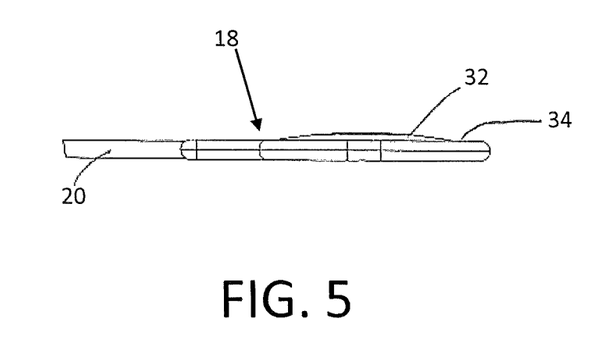
FIG. 5 illustrates a side view of the distal end of the lens injector illustrated in FIG. 3.
Figure 6:
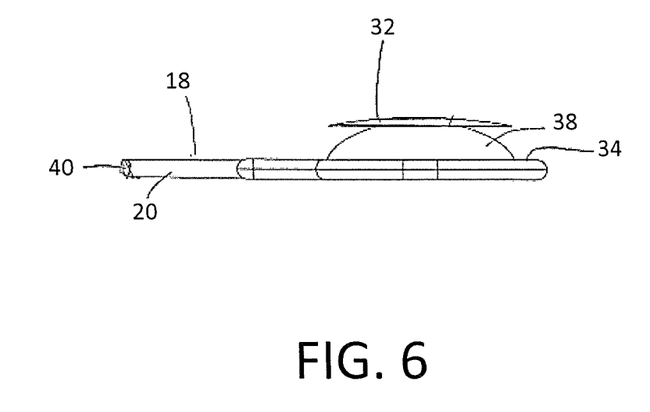
FIG. 6 illustrates a side view of the distal end of the lens injector illustrated in FIG. 4.

FIGS. 5 and 6 illustrates a side view of the distal end of the lens injector illustrated in FIGS. 3 and 4. As shown in FIGS. 5 and 6 the paddle arm 20 defines a lumen 40 extending therethrough. The lumen 40 at the proximal end 42 of the paddle arm 20 is in fluid communication with the syringe 12 and the lumen 40 at the distal end 22 of the paddle arm 20 is in fluid communication with the paddle 18. The proximal end of the paddle 18 is coupled to the distal end 22 of the paddle arm 20 such that a fluid flow path is created from the syringe 12 to the paddle 18. . FIG. 5 further illustrates the lens injector 10 in its resting, loaded state. The lens 32 is disposed on a top surface 34 of the paddle 18. The paddle 18 can be configured such that the lens 32 nests within a depression 36 on the top surface 34 of the paddle 18. FIG. 6 further illustrates the lens injector 10 after the plunger 26 has been depressed. As the plunger 26 is depressed, saline is dispensed on the top surface 34 of the paddle 18. The saline flows through the fluid flow path created from the syringe 12 to the paddle 18. This forms a saline droplet 38 on the top surface 34 of the paddle 18, lifting the lens 32 off of the top surface 34 of the paddle 18.

Figures 7, 8:
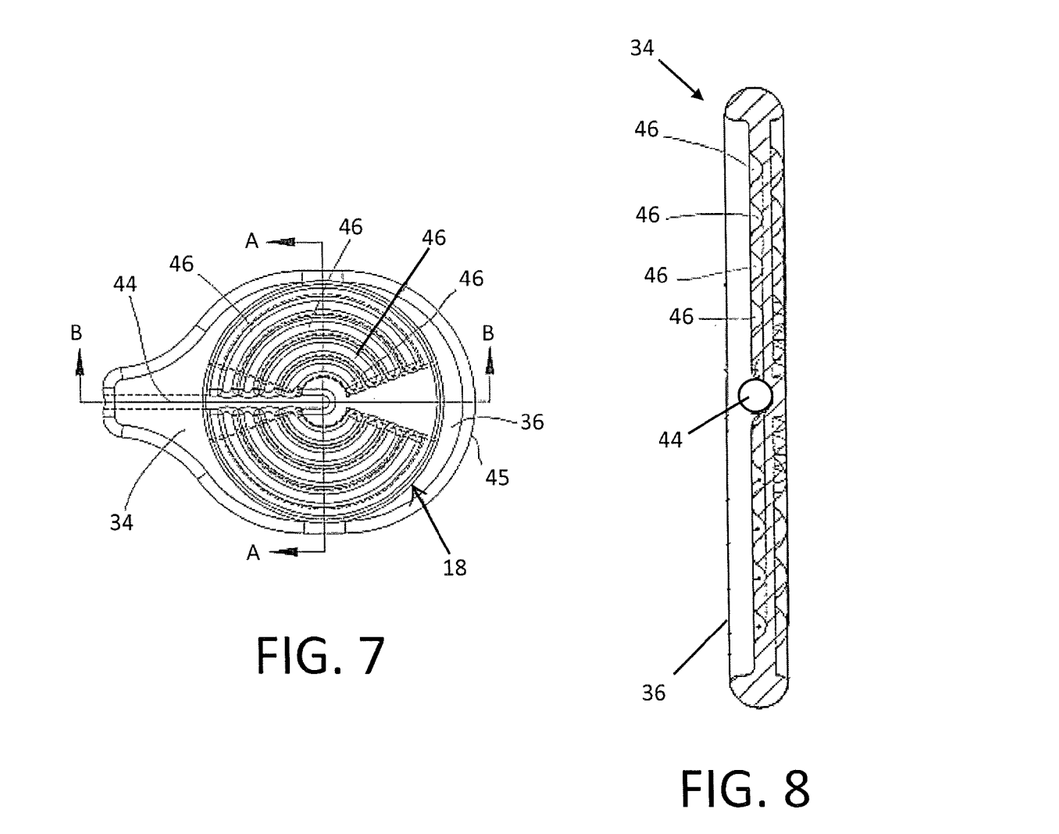
FIG. 7 illustrates a top view of a paddle of a lens injector in accordance with an embodiment of the invention.
FIG. 8 illustrates a sectional view taken along axis A of a paddle of a lens injector illustrated in FIG. 7.

FIG. 7 illustrates a top view of a paddle of a lens injector in accordance with an embodiment of the invention. As shown in FIG. 7, a fill channel 44 preferably extends into at least a portion of the length of the paddle 18. Alternately the fill channel 44 can extend to near a proximal end 45 of the paddle 18. Preferably the fill channel has a width in a range of 0.3 mm to 1.0 mm. The paddle 18 also can include a flood channel 46 extending around at least a portion of a circumference of the paddle 18. As illustrated in FIG. 7, there can also be multiple flood channels 46 positioned concentrically, over the top surface 34 of the paddle 18. Preferably, the flood channel 46 has a width in a range of 0.1 mm to 0.3 mm. The fill channel 44 can be in fluid communication with the flood channels 46, such that when saline flows through the fill channel 44 it then flows into the flood channels 46. As the fill channel 44 fills the flood channels 46, the saline Balanced Salt Solution (BSS) or droplet shown in FIGS. 2, 4, and 6 can be formed.

Figure 9:
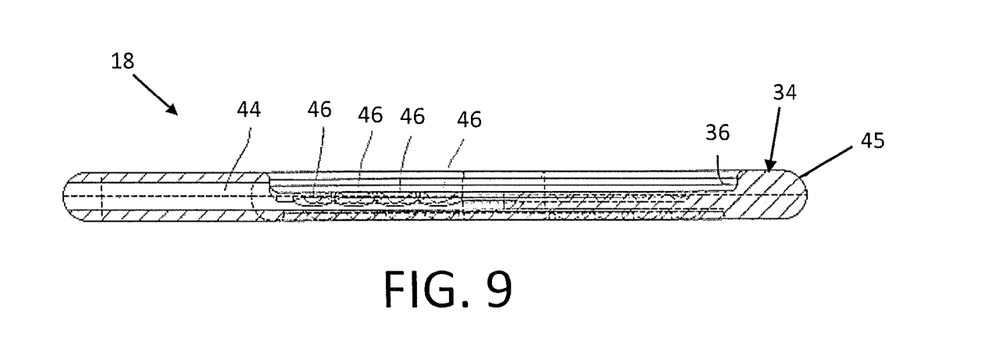
FIG. 9 illustrates a sectional view taken along axis B of a paddle of a lens injector illustrated in FIG. 7.

FIGS. 8 and 9 illustrate sectional views taken along axis A and B, respectively, of a paddle of a lens injector illustrated in FIG. 7. FIGS. 8 and 9 show depression 36 in the top surface 34 of the paddle 18. The lens 32 can then be positioned in the depression 36 of the paddle. Preferably, the depression 36 has a depth in a range of 0.05 mm to 0.1 mm. The fill channel 44 preferably extends into at least a portion of the length of the paddle 18. Alternately the fill channel 44 can extend to near a proximal end 45 of the paddle 18. Preferably the fill channel has a width in a range of 0.3 mm to 1.0 mm and a depth in a range of 0.1 mm to 0.3 mm. The paddle 18 also can include the flood channel 46 extending around at least a portion of a circumference of the paddle 18. There can also be multiple flood channels 46 positioned concentrically, over the top surface 34 of the paddle 18. Preferably, the flood channel 46 has a width in a range of 0.3 mm to 0.5 mm and a depth in a range of 0.1 mm to 0.3 mm The fill channel 44 can be in fluid communication with the flood channels 46, such that when Balanced Salt Solution (BSS) or saline flows through the fill channel 44 it then flows into the flood channels 46. As the fill channel 44 fills the flood channels 46, the saline droplet shown in FIGS. 2, 4, and 6 can be formed.

Figure 10:
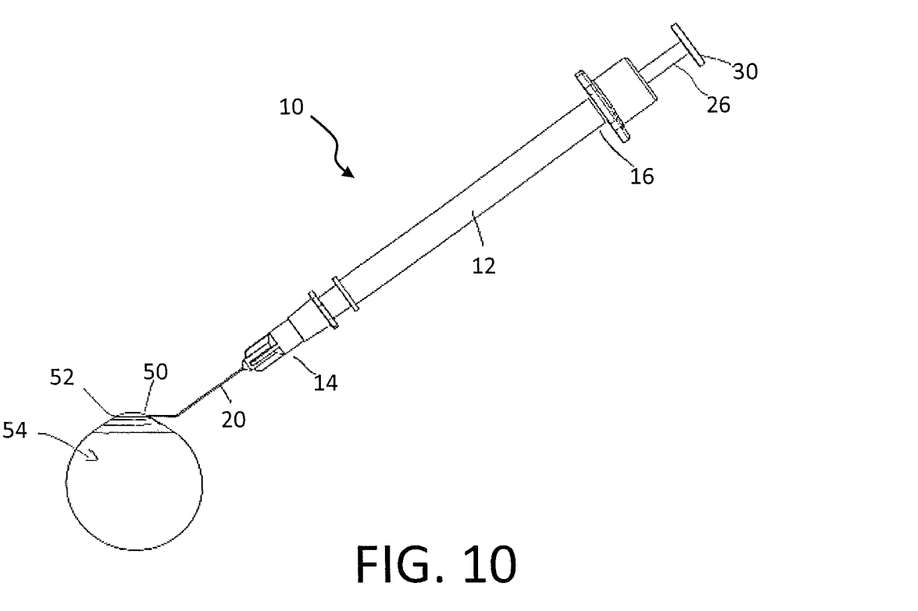
FIG. 10 a top view of a lens injector apparatus in accordance with an embodiment of the invention.
Figure 11:
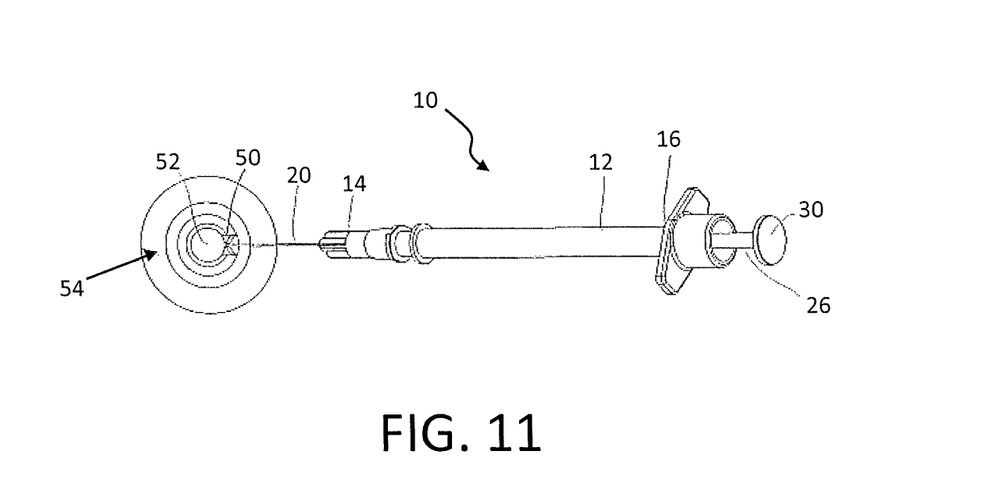
FIG. 11 a side view of a lens injector apparatus in accordance with an embodiment of the invention.

FIGS. 10 and 11 illustrate a top view of a lens injector apparatus in accordance with an embodiment of the invention and a side view of a lens injector apparatus in accordance with an embodiment of the invention, respectively. FIGS. 10 and 11 show the injector 10 being used to insert the lens 32 (not shown) into a pocket 50 in a cornea 52 of an eye 54. The paddle arm 20 injector 10 includes the angle α, which is in the range of 15° to 30°. The angle α can also be any angle configured to insert the paddle 18 into the pocket 50 of the cornea 52.

Figure 12:
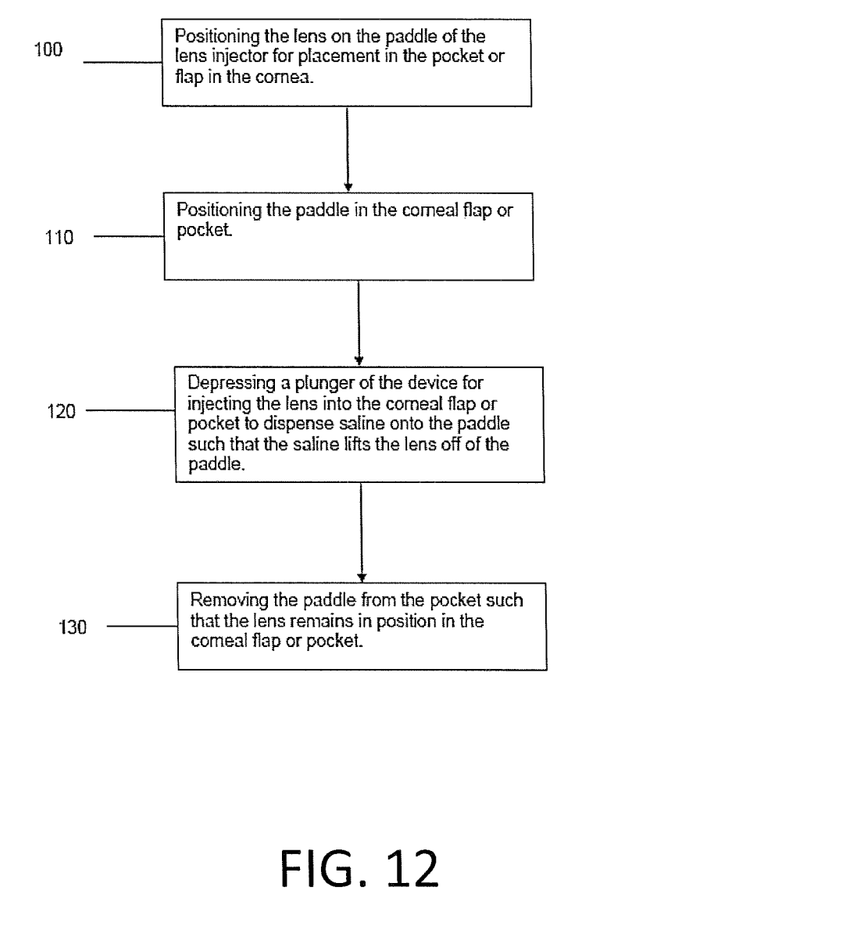
FIG. 12 illustrates a method of inserting a lens using a lens injector apparatus in accordance with an embodiment of the invention.

FIG. 12 illustrates a method of inserting a lens into a pocket or flap in a cornea in accordance with an embodiment of the invention. Step 100 includes positioning the lens 32 on the paddle of the lens injector 10 for placement in the pocket or flap in the cornea. Preferably, the lens 32 is approximately 2.5 mm to 3.5 mm in diameter and has an edge thickness of less than 20 microns. Any lens suitable for insertion into a pocket or flap in a cornea can be used. In step 110, the paddle can be positioned in the corneal flap or pocket. Step 120 includes depressing a plunger of the device for injecting the lens into the corneal flap or pocket to dispense Balanced Salt Solution (BSS) or saline onto the paddle such that the saline lifts the lens off of the paddle. In step 130, the paddle can be removed from the pocket, such that the lens remains in position in the corneal flap or pocket.

The many features and advantages of the invention are apparent from the detailed specification, and thus, it is intended by the appended claims to cover all such features and advantages of the invention, which fall within the true spirit, and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An apparatus for injecting a lens into an eye comprising:
   a syringe having a distal: end and a proximal end and an outer wall of the syringe defining a lumen extending through the syringe and wherein the lumen of the syringe is configured to hold fluid, balanced salt solution (BSS) or saline;
   a plunger extending movably through the lumen of the syringe having a distal end and a proximal end and configured to eject the fluid, balanced salt solution (BBS) or saline from the lumen of the syringe;
   a paddle arm defining a lumen extending from the distal end of the syringe, wherein the paddle arm includes a bend of between an angle of 100° and 160°; and
   a paddle coupled to the paddle arm distally of the bend, the paddle having a lower surface and a parallel top surface being clear of a corresponding opposed structure and the top surface having a depression extending towards the lower surface configured to hold the lens to be inserted into the eye, wherein a fluid flow path is defined through the paddle and the lumen defined by the paddle arm, the fluid flow path being in fluid communication with the lumen of the syringe and configured to allow the fluid, balanced salt solution (BBS) or saline to flow onto a plurality of circumferentially arranged flood channels on the depression of the paddle to lift the lens off from the top surface of the paddle such that the lens can be positioned in the eye.

2. The apparatus of claim 1 wherein the paddle comprises a fill channel defining the fluid flow path on the paddle.

3. The apparatus of claim 2, wherein the fill channel is configured to extend to one or more of the plurality of circumferentially arranged flood channel channels such that the fill channel and one or more of the plurality of circumferentially arranged flood channels are in fluid communication.

4. The apparatus of claim 2, wherein the fill channel is configured to extend through the plurality of circumferentially arranged flood channels such that the fill channel is in fluid communication with each of the plurality of circumferentially arranged flood channels individually.

5. The apparatus of claim 1 wherein the depression of the top surface of the paddle includes a concave depression configured such that the lens nests in the top surface of the paddle during insertion.

6. An apparatus for injecting a lens into a corneal pocket or flap comprising:
   a handle having a distal end and a proximal end and an outer wall of the handle defining a lumen extending through the handle;
   a plunger extending movably through the lumen of the handle having a distal end and a proximal end; and
   a paddle having a proximal end and a distal end extending from the distal end of the handle comprising: a tubular portion positioned at the proximal end of the paddle, wherein the tubular portion defines a bend of between 100° and 160° and an inner lumen in fluid communication with the inner lumen of the handle; a disc portion having lower surface and a parallel top surface being clear of a corresponding opposed structure and the top surface including a depression extending towards the lower surface configured to hold the lens to be inserted into the eye, wherein the disc portion is in fluid communication with the tubular portion; and wherein the paddle is configured to allow fluid, balanced salt solution (BSS) or saline to flow onto a plurality of circumferentially arranged flood channels on the depression of the top surface of the disc portion of the paddle used to lift the lens off from the top surface such that the lens can be released in the corneal pocket or flap.

7. The apparatus of claim 6 wherein the paddle comprises a fill channel defining the fluid flow path on the paddle.

8. The apparatus of claim 7 wherein the fill channel is configured to extend to one or more of the plurality of circumferentially arranged flood channels such that the fill channel and one or more of the plurality of flood channels are in fluid communication.

9. The apparatus of claim 7 wherein the fill channel is configured to extend through the plurality of circumferentially arranged flood channels such that the fill channel is in fluid communication with each of the plurality of circumferentially arranged flood channels individually.

10. The apparatus of claim 6 wherein the depression of the too surface of the paddle includes a concave depression configured such that the lens nests in the top surface of the paddle during insertion.

11. A method for injecting a lens into a corneal pocket or flap comprising;
    positioning the lens on a depression of a top surface extending towards a substantially parallel lower surface of a paddle, the top surface being clear from a corresponding opposed structure and the depression including a plurality of circumferentially arranged flood channels, and the paddle is disposed at a distal end of a device for injecting the lens into the corneal flap or pocket, wherein the distal end of the device includes a bend of between 100° and 160° proximal of the paddle;
    directing the paddle with the lens into a corneal flap or pocket;
    positioning the paddle in the corneal flap or pocket;
    depressing a plunger of the device for injecting the lens into the corneal flap or pocket to dispense fluid, balanced salt solution (BBS) or saline onto one or more of the plurality of circumferentially arranged flood channels such that the fluid, balanced salt solution (BSS) or saline lifts the lens off the depression of the top surface of the paddle; and
    removing the paddle from the corneal flap or pocket, such that the lens remains in position in the corneal flap or pocket.

12. The method of claim 11 further comprising filling a fill channel defined by the paddle with fluid, balanced salt solution (BSS) or saline.

13. The method of claim 11 further comprising nesting the lens on the top surface in the depression of the paddle.

14. The method of claim 11 further comprising creating a fluid, balanced salt solution (BBS) or saline droplet on the top surface of the paddle between the top surface of the paddle and the lens.

* * * * *